US009642671B2

(12) United States Patent
Lee et al.

(10) Patent No.: US 9,642,671 B2
(45) Date of Patent: May 9, 2017

(54) LIMITED-USE MEDICAL DEVICE

(71) Applicant: COVIDIEN LP, Mansfield, MA (US)

(72) Inventors: Weng-Kai K. Lee, Longmont, CO (US); Christopher A. Deborski, Denver, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 333 days.

(21) Appl. No.: 14/335,303

(22) Filed: Jul. 18, 2014

(65) Prior Publication Data

US 2015/0094714 A1    Apr. 2, 2015

Related U.S. Application Data

(60) Provisional application No. 61/884,558, filed on Sep. 30, 2013.

(51) Int. Cl.
| | |
|---|---|
| A61B 18/14 | (2006.01) |
| A61B 17/29 | (2006.01) |
| A61B 17/072 | (2006.01) |
| A61B 17/00 | (2006.01) |
| A61B 18/00 | (2006.01) |

(Continued)

(52) U.S. Cl.
CPC .... *A61B 18/1445* (2013.01); *A61B 17/07207* (2013.01); *A61B 17/2909* (2013.01); *A61B 17/28* (2013.01); *A61B 17/29* (2013.01); *A61B 2017/0023* (2013.01); *A61B 2017/2931* (2013.01); *A61B 2018/00059* (2013.01); *A61B 2018/00065* (2013.01);

(Continued)

(58) Field of Classification Search
CPC ... A61B 17/07207; A61B 17/28; A61B 17/29; A61B 17/2909; A61B 18/1445; A61B 2017/0023; A61B 2017/2931; A61B 2017/0059; A61B 2017/0065; A61B 2017/1457; A61B 2090/081; A61B 2090/0814; A61F 2250/009
See application file for complete search history.

(56) References Cited

U.S. PATENT DOCUMENTS

| | | |
|---|---|---|
| 3,678,229 A | 7/1972 | Osika |
| 4,016,881 A | 4/1977 | Rioux et al. |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

U.S. Appl. No. 08/926,869, filed Sep. 10, 1997, James G. Chandler.

(Continued)

*Primary Examiner* — Daniel Fowler

(57) ABSTRACT

A medical device including one or more components positioned to contact contaminants during use of the medical device. The one or more components including one or more limited-use portions transitionable upon use from an initial state, wherein the limited-use portion(s) exhibits a clean appearance, to a used state, wherein the limited-use portion(s) exhibits a contaminated appearance that visually indicates to a user that the at least one component is not further usable.

15 Claims, 7 Drawing Sheets

(51) Int. Cl.
*A61B 17/28* (2006.01)
*A61B 90/00* (2016.01)

(52) U.S. Cl.
CPC . *A61B 2018/1457* (2013.01); *A61B 2090/081* (2016.02); *A61B 2090/0814* (2016.02); *A61F 2250/009* (2013.01)

(56) References Cited

U.S. PATENT DOCUMENTS

| | | |
|---|---|---|
| D249,549 S | 9/1978 | Pike |
| 4,311,145 A | 1/1982 | Esty et al. |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| 4,781,683 A | 11/1988 | Wozniak et al. |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| 5,359,993 A | 11/1994 | Slater et al. |
| D354,564 S | 1/1995 | Medema |
| D358,887 S | 5/1995 | Feinberg |
| D384,413 S | 9/1997 | Zlock et al. |
| 5,700,270 A | 12/1997 | Peyser et al. |
| 5,779,699 A * | 7/1998 | Lipson .............. A61B 18/1492 606/41 |
| H1745 H | 8/1998 | Paraschac |
| 5,814,043 A | 9/1998 | Shapeton |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,994,707 B2 | 2/2006 | Ellman et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| 7,176,030 B2 | 2/2007 | Faries, Jr. et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,244,252 B2 | 7/2007 | Berndt |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,132,086 B2 | 3/2012 | Park et al. |
| D661,394 S | 6/2012 | Romero et al. |
| 8,522,626 B2 | 9/2013 | Woodcock |
| 8,535,311 B2 | 9/2013 | Schall |
| 8,540,712 B2 | 9/2013 | Mueller |
| 8,546,999 B2 | 10/2013 | Houser et al. |
| 8,579,177 B2 | 11/2013 | Beetel |
| 8,679,140 B2 | 3/2014 | Butcher |
| RE44,834 E | 4/2014 | Dumbauld et al. |
| 8,702,237 B2 | 4/2014 | Heacock et al. |
| 2002/0165549 A1 | 11/2002 | Owusu-Akyaw et al. |
| 2006/0069305 A1* | 3/2006 | Couvillon, Jr. .... A61B 1/00055 600/117 |
| 2009/0065565 A1 | 3/2009 | Cao |
| 2010/0280511 A1 | 11/2010 | Rachlin et al. |
| 2011/0009859 A1 | 1/2011 | Livneh |
| 2011/0306972 A1 | 12/2011 | Widenhouse et al. |
| 2012/0191091 A1* | 7/2012 | Allen ................ A61B 18/1206 606/52 |
| 2012/0205419 A1 | 8/2012 | Weir et al. |
| 2012/0248167 A1 | 10/2012 | Flanagan et al. |
| 2013/0018371 A1 | 1/2013 | Twomey |
| 2013/0046303 A1 | 2/2013 | Evans et al. |
| 2013/0181033 A1 | 7/2013 | Shelton, IV et al. |
| 2013/0186933 A1 | 7/2013 | Shelton, IV et al. |
| 2013/0245623 A1 | 9/2013 | Twomey |
| 2013/0247343 A1 | 9/2013 | Horner et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0267950 A1 | 10/2013 | Rosa et al. |
| 2013/0274736 A1 | 10/2013 | Garrison |
| 2013/0282010 A1 | 10/2013 | McKenna et al. |
| 2013/0282024 A1 | 10/2013 | Blumenkranz |
| 2013/0289558 A1 | 10/2013 | Reid, Jr. et al. |
| 2013/0289559 A1 | 10/2013 | Reid, Jr. |
| 2013/0289560 A1 | 10/2013 | DeCarlo et al. |
| 2013/0289561 A1 | 10/2013 | Waaler et al. |
| 2013/0296848 A1 | 11/2013 | Allen, IV et al. |
| 2013/0296854 A1 | 11/2013 | Mueller |
| 2013/0296856 A1 | 11/2013 | Unger et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |
| 2014/0031821 A1 | 1/2014 | Garrison |
| 2014/0031860 A1 | 1/2014 | Stoddard et al. |
| 2014/0046323 A1 | 2/2014 | Payne et al. |
| 2014/0066910 A1 | 3/2014 | Nau, Jr. |
| 2014/0066911 A1 | 3/2014 | Nau, Jr. |
| 2014/0074091 A1 | 3/2014 | Arya et al. |

(56) References Cited

U.S. PATENT DOCUMENTS

| | | |
|---|---|---|
| 2014/0100564 A1 | 4/2014 | Garrison |
| 2014/0100568 A1 | 4/2014 | Garrison |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02045589 A3 | 9/2002 |
| WO | 2006/021269 A1 | 3/2006 |
| WO | 2005110264 A3 | 4/2006 |
| WO | 2008/040483 A1 | 4/2008 |
| WO | 2011/018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Schmaltz.
U.S. Appl. No. 09/591,328, filed Jun. 9, 2000, Ryan.
U.S. Appl. No. 12/336,970, filed Dec. 17, 2008, Sremcich.
U.S. Appl. No. 13/731,674, filed Dec. 31, 2012, Siebrecht.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

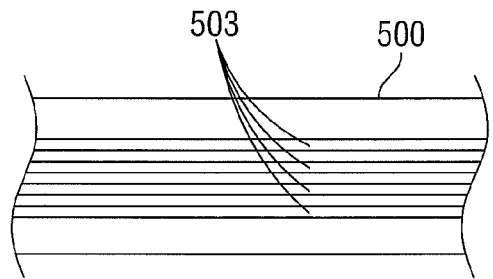
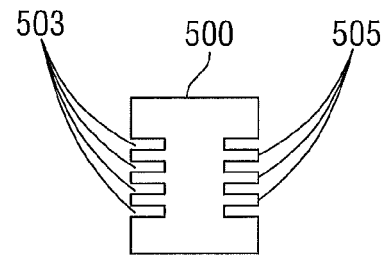
FIG. 5A          FIG. 5B
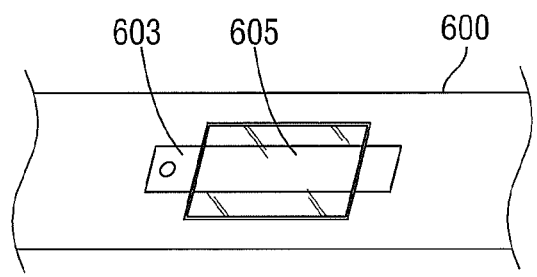
FIG. 6
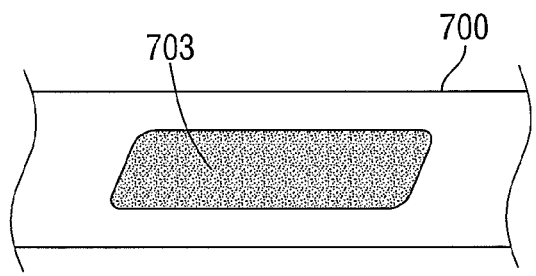
FIG. 7

LIMITED-USE MEDICAL DEVICE

CROSS REFERENCE TO RELATED APPLICATION

The present application claims the benefit of and priority to U.S. Provisional Application Ser. No. 61/884,558, filed on Sep. 30, 2013, the entire contents of which are incorporated herein by reference.

BACKGROUND

Technical Field

The present disclosure relates to medical devices. More particularly, the present disclosure is directed to limited-use medical devices and medical devices including limited-use portions.

Background of the Related Art

Certain medical devices (or components thereof) are capable of being used multiple times, and are thus referred to as reusable devices (or reusable components), while other medical devices (or components thereof) are configured for single use, and are thus referred to as disposable devices (or disposable components). Many such reusable and disposable medical devices, and/or the components thereof, are designed for a pre-determined number of uses and/or for a pre-determined usage time. Use of these devices beyond their prescribed usage time or number of uses may result in failure of the device, damage to the device or surrounds, and/or injury to the patient or clinician. On the other hand, given the rising costs of performing medical procedures, clinician's have an incentive to maximize the reuse of medical devices (or components thereof).

SUMMARY

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure. To the extent consistent, any of the aspects and features described herein may be used in conjunction with any or all of the other aspects and features described herein.

In accordance with an aspect of the present disclosure, a medical device may include at least one component positioned to contact contaminants during use of the medical device, the at least one component including at least one limited-use portion, the limited-use portion transitionable upon use from an initial state, wherein the limited-use portion exhibits a clean appearance, to a used state, wherein the limited-use portion exhibits a contaminated appearance that visually indicates to a user that the at least one component is not further usable.

In accordance with another aspect of the disclosure herein, the at least one component may be a jaw member of a surgical forceps.

In accordance with another aspect of the disclosure herein, the at least one component may be a disposable electrode assembly.

In accordance with another aspect of the disclosure herein, the disposable electrode assembly may be configured to conduct electrosurgical energy to tissue.

In accordance with another aspect of the disclosure herein, the at least one component may be a housing of an endoscopic medical device.

In accordance with another aspect of the disclosure herein, the at least one limited-use portion may be a contamination trap.

In accordance with another aspect of the disclosure herein, the contamination trap may include a plurality of grooves configured to trap bodily fluids and tissue remnants.

In accordance with another aspect of the disclosure herein, the contamination trap may have a window disposed thereon configured to allow a user to view contaminants within the contamination trap.

In accordance with another aspect of the disclosure herein, the contamination trap may include at least one indicator for indicating that the contamination trap is contaminated.

In accordance with another aspect of the disclosure herein, the at least one limited-use portion may be a color change material configured to exhibit a contaminated appearance in the used state.

In accordance with another aspect of the disclosure herein, the color change may be effected via contact of the at least one limited-use portion with at least one of blood, tissue, and fluids.

In accordance with another aspect of the disclosure herein, the color change material may be temperature-sensitive.

In accordance with another aspect of the disclosure herein, a method may include providing a medical device including at least one component, using the medical device to perform a surgical task, wherein, during use of the medical device, the at least one component comes into contact with contaminants, and visually displaying to a user an indication that the at least one component is not further usable after use of the medical device.

In accordance with another aspect of the disclosure herein, upon use of the medical device, at least one limited-use portion of the at least one component may be transitioned from an initial state, wherein the limited-use portion exhibits a clean appearance, to a used state, wherein the limited-use portion exhibits a contaminated appearance that visually indicates to the user that the at least one component is not further usable.

In accordance with another aspect of the disclosure herein, the at least one limited-use portion may be a contamination trap including a plurality of grooves configured to trap of bodily fluids and tissue remnants.

In accordance with another aspect of the disclosure herein, the contamination trap may have a window disposed thereon configured to allow a user to view contaminants within the contamination trap.

In accordance with another aspect of the disclosure herein, the contamination trap may include at least one indicator for indicating that the contamination trap is contaminated.

In accordance with another aspect of the disclosure herein, the at least one limited-use portion may be a color change material configured to exhibit a contaminated appearance in the used state.

In accordance with another aspect of the disclosure herein, the color change may be effected via contact of the at least one limited-use portion with at least one of blood, tissue, and fluids.

BRIEF DESCRIPTION OF THE DRAWINGS

The above and other aspects, features, and advantages of the present disclosure will become more apparent in light of the following detailed description when taken in conjunction with the accompanying drawings, wherein:

FIG. 5A is an enlarged, side view of a limited-use portion provided in accordance with the present disclosure and configured for incorporation into any of the medical devices or end effector assemblies of FIGS. 1-4B;

FIG. 5B is an enlarged, cross-sectional view of the limited-use portion of FIG. 5A;

FIG. 6 is an enlarged, side view of another limited-use portion provided in accordance with the present disclosure and configured for incorporation into any of the medical devices or end effector assemblies of FIGS. 1-4B;

FIG. 7 is an enlarged, side view of another limited-use portion provided in accordance with the present disclosure and configured for incorporation into any of the medical devices or end effector assemblies of FIGS. 1-4B.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
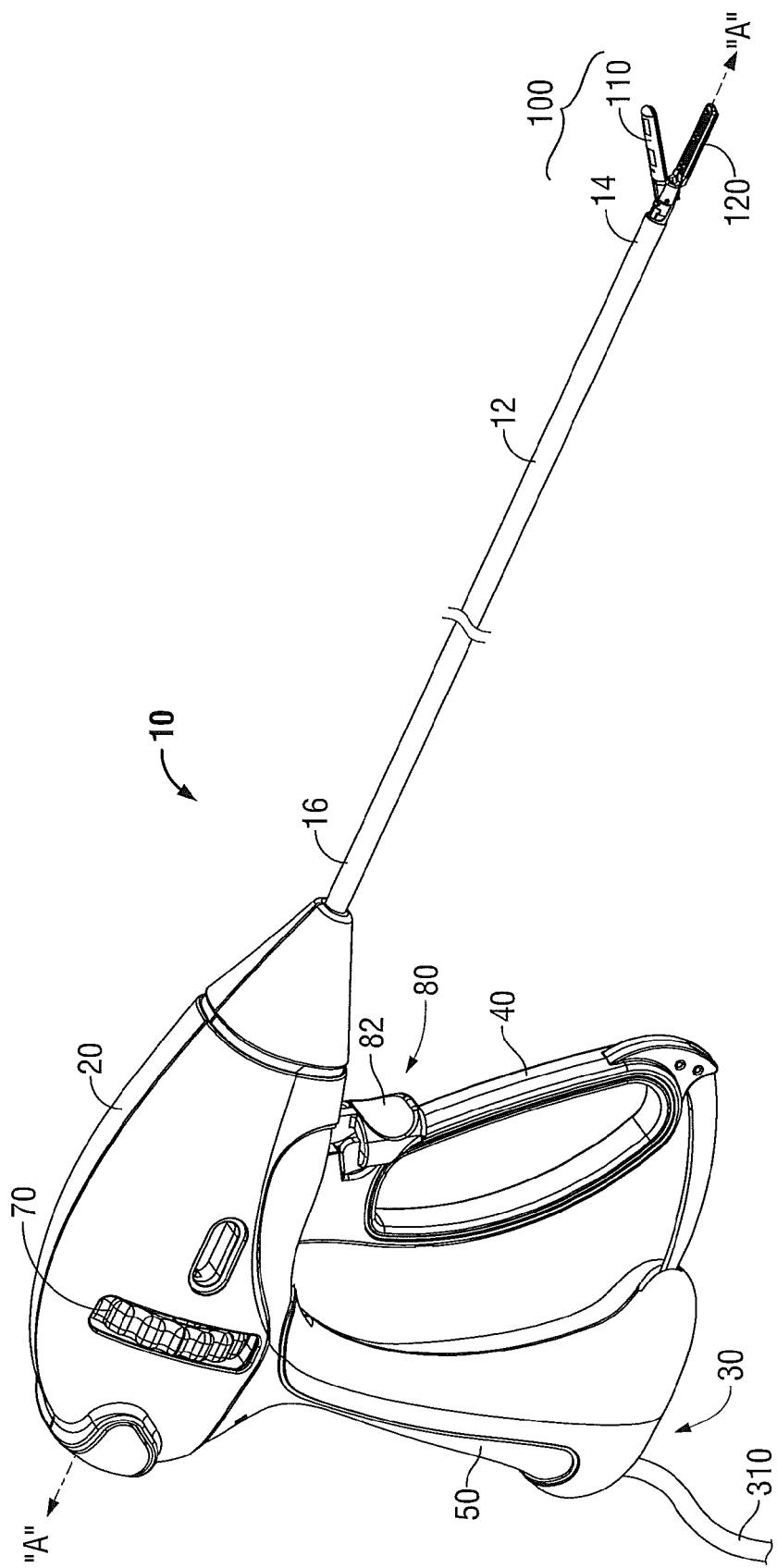
FIG. 1 is a perspective view of a medical device provided in accordance with the present disclosure.

Referring now to FIG. 1, a forceps 10 for use in connection with endoscopic surgical procedures is shown, although forceps 10 may also be configured for use in connection with traditional open surgical procedures. Alternatively, the present disclosure may be embodied in any other suitable medical devices such as, but not limited to scissors, staplers, probes, syringes, and any other electrical, mechanical, or electromechanical medical devices.

Continuing with reference to FIG. 1, forceps 10 defines a longitudinal axis "A-A" and includes a housing 20, a handle assembly 30, a rotating assembly 70, a trigger assembly 80 and an end effector assembly 100. End effector assembly 100 includes first and second jaw members 110, 120, respectively, configured to pivot relative to one another between a spaced-apart position and an approximated position for grasping tissue therebetween. Forceps 10 further includes a shaft 12 having a distal end 14 configured to mechanically engage end effector assembly 100 and a proximal end 16 that mechanically engages housing 20. Forceps 10 also includes a cable 310 that connects forceps 10 to a generator (not shown) or other suitable power source, although forceps 10 may alternatively be configured as a battery powered instrument. Cable 310 includes wires extending therethrough and into housing 20 to ultimately connect the source of energy (not shown) to tissue-contacting surfaces 216, 226 (FIG. 2) of jaw members 110, 120, respectively, to conduct energy therebetween and through tissue grasped between jaw members 110, 120 to treat tissue. As disclosed above, the medical device is described herein as an electrosurgical forceps 10, however, the medical device may also be a mechanical forceps or other medical device or a device with electrical or moving parts.

With continued reference to FIG. 1, handle assembly 30 includes a fixed handle 50 and a moveable handle 40. Fixed handle 50 is integrally associated with housing 20 and handle 40 is moveable relative to fixed handle 50. Rotating assembly 70 is rotatable in either direction about a longitudinal axis "A-A" to rotate end effector assembly 100 about longitudinal axis "A-A." The housing 20 houses the internal working components of the forceps 10.

Figure 2:
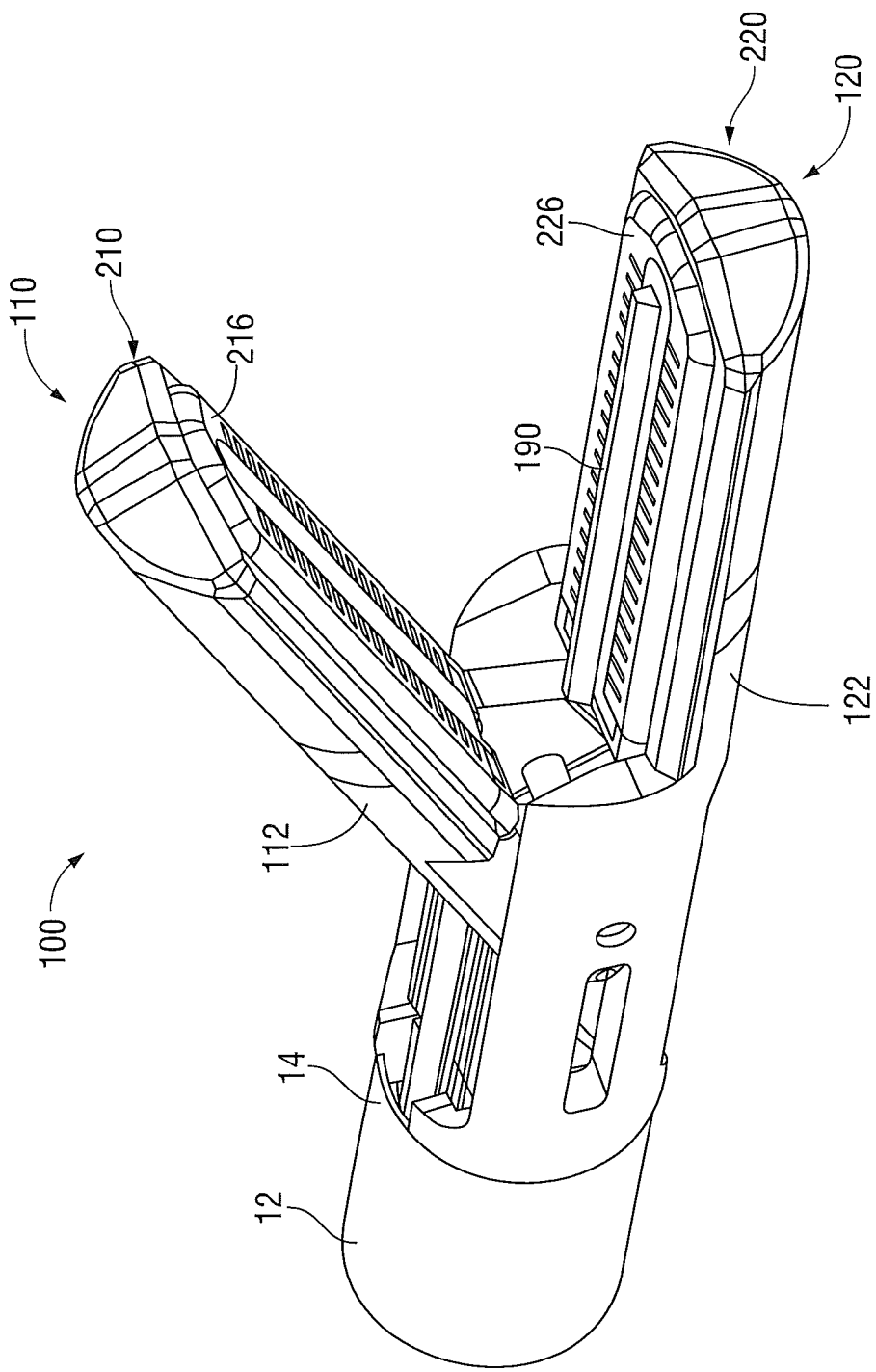
FIG. 2 is a perspective view of an end effector assembly provided in accordance with the present disclosure and configured for use with the medical device of FIG. 1.

Referring FIG. 2, end effector assembly 100 is shown attached at a distal end 14 of shaft 12 and includes a pair of opposing jaw members 110 and 120. Each of the first and second jaw members 110, 120 includes a fixed jaw frame 112, 122, respectively, and a replaceable component 210, 220, respectively, selectively engagable with the respective jaw frame 112, 122 to form the fully assembled jaw members 110, 120, respectively. However, jaw members 110, 120 of end effector assembly 100 may also be configured as integral components, e.g., wherein components 210, 220 are fixedly engaged or otherwise integrated with jaw frames 112, 122 of jaw members 110, 120, respectively.

End effector assembly 100 is designed as a unilateral assembly, i.e., where jaw member 120 is fixed relative to shaft 12 and jaw member 110 is moveable relative to both shaft 12 and fixed jaw member 120. However, end effector assembly 100 may alternatively be configured as a bilateral assembly, i.e., where both jaw member 110 and jaw member 120 are moveable relative to one another and with respect to shaft 12.

Each jaw member 110, 120 defines an electrically conductive tissue-contacting surface 216, 226 configured to connect to the energy source (not shown), e.g., via the wires of cable 310 (FIG. 1), for conducting energy therebetween and through tissue grasped between jaw members 110, 120 to treat tissue. In some embodiments, a knife assembly (not shown) is disposed within shaft 12 and a knife channel (not shown) is defined within one or both of jaw members 110, 120, respectively, to permit reciprocation of a knife blade (not shown) therethrough for mechanically cutting tissue grasped between jaw members 110, 120. In such an embodiment, trigger 82 of trigger assembly 80 (see FIG. 1) is operable to advance the knife blade (not shown) between a retracted position, wherein the knife blade (not shown) is disposed within shaft 12, and an extended position, wherein the knife blade (not shown) extends between jaw members 110, 120 to cut tissue grasped therebetween. End effector assembly 100 may also be adapted for electrical cutting via an electrical cutting insert 190 connected to the source of energy (not shown), e.g., via the wires of cable 310 (FIG. 1), thus obviating the need for a knife assembly (not shown).

Further, end effector assembly 100 may be adapted for both mechanical cutting and electrical cutting, thus allowing a user to select a mode of operation best suited for the particular surgical procedure to be performed.

Referring again to FIG. 1, moveable handle 40 of handle assembly 30 is ultimately connected to a drive assembly (not explicitly shown) that, together, mechanically cooperate to impart movement of jaw members 110 and 120 between a spaced-apart position and an approximated position to grasp tissue between tissue-contacting surfaces 216 and 226 of jaw members 110, 120, respectively. As shown in FIG. 1, moveable handle 40 is initially spaced-apart from fixed handle 50 and, correspondingly, jaw members 110, 120 are disposed in the spaced-apart position. Moveable handle 40 is compressible from this initial position to a compressed position corresponding to the approximated position of jaw members 110, 120.

With reference generally to FIGS. 3A-8, various embodiments of medical devices, or components thereof, are shown including one or more limited-use portions. Generally, these limited-use portions are configured to alert the user that the device (or component thereof) is not to be used further or cannot be used further. The alert scheme may be a visual alert, a tactile alert, and audio alert, any other suitable alert scheme, or any combination thereof. For example, these limited-use portions may be configured for a single use such that, after performing a medical procedure, the medical devices incorporating such limited-use portions are noticeably contaminated or appear contaminated such that the user is alerted to perceived issues of reuse. Further, although the limited-use portions are described below as being incorporated into different components and/or features of particular example medical devices to inhibit reuse of these medical devices, it is contemplated that the limited-used portions be incorporated, attached, or otherwise coupled to any suitable component(s) of any suitable medical device for similar purposes.

Figure 3A:
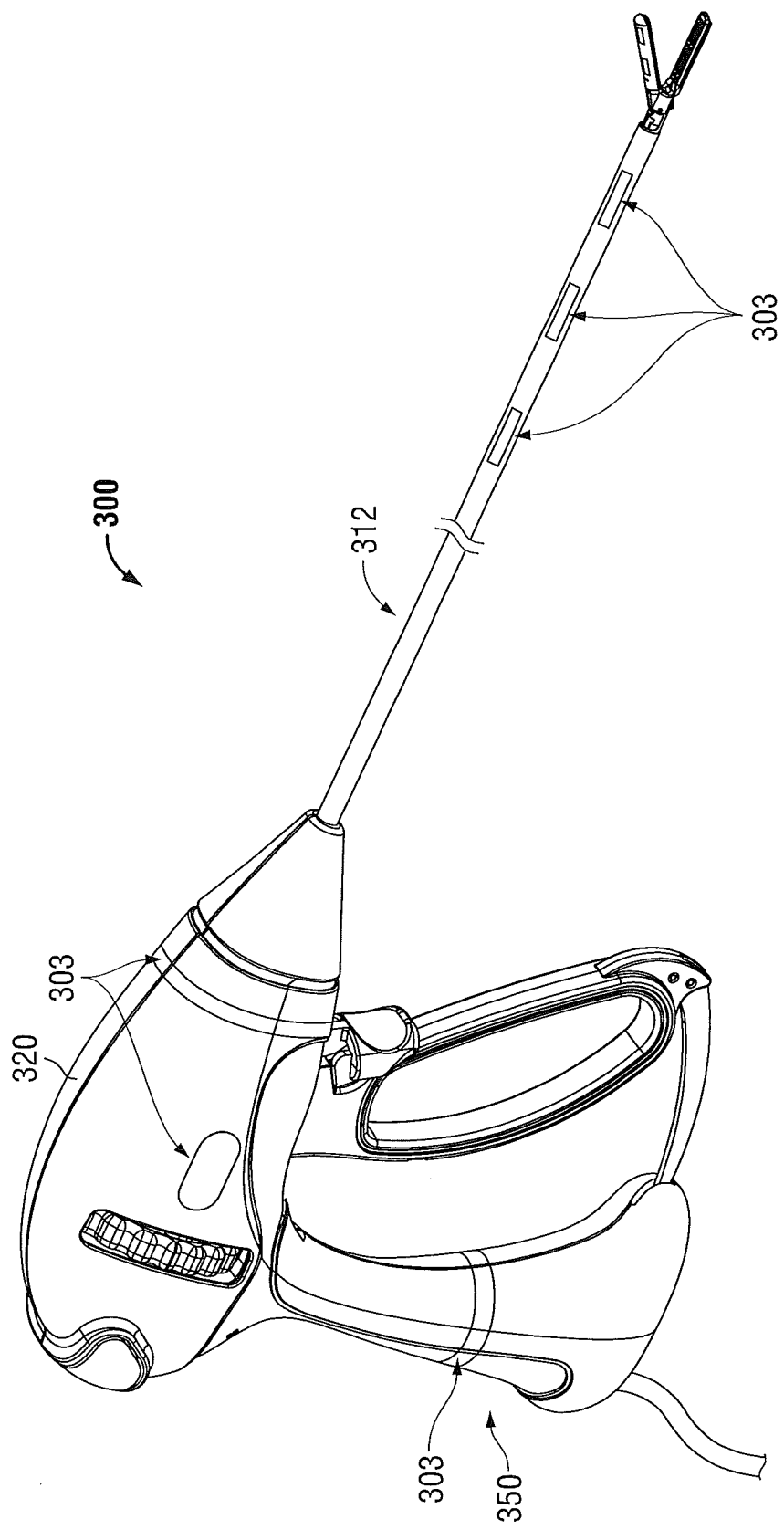
FIG. 3A is a perspective view of another a medical device provided in accordance with the present disclosure, shown in an unused condition.
Figure 3B:
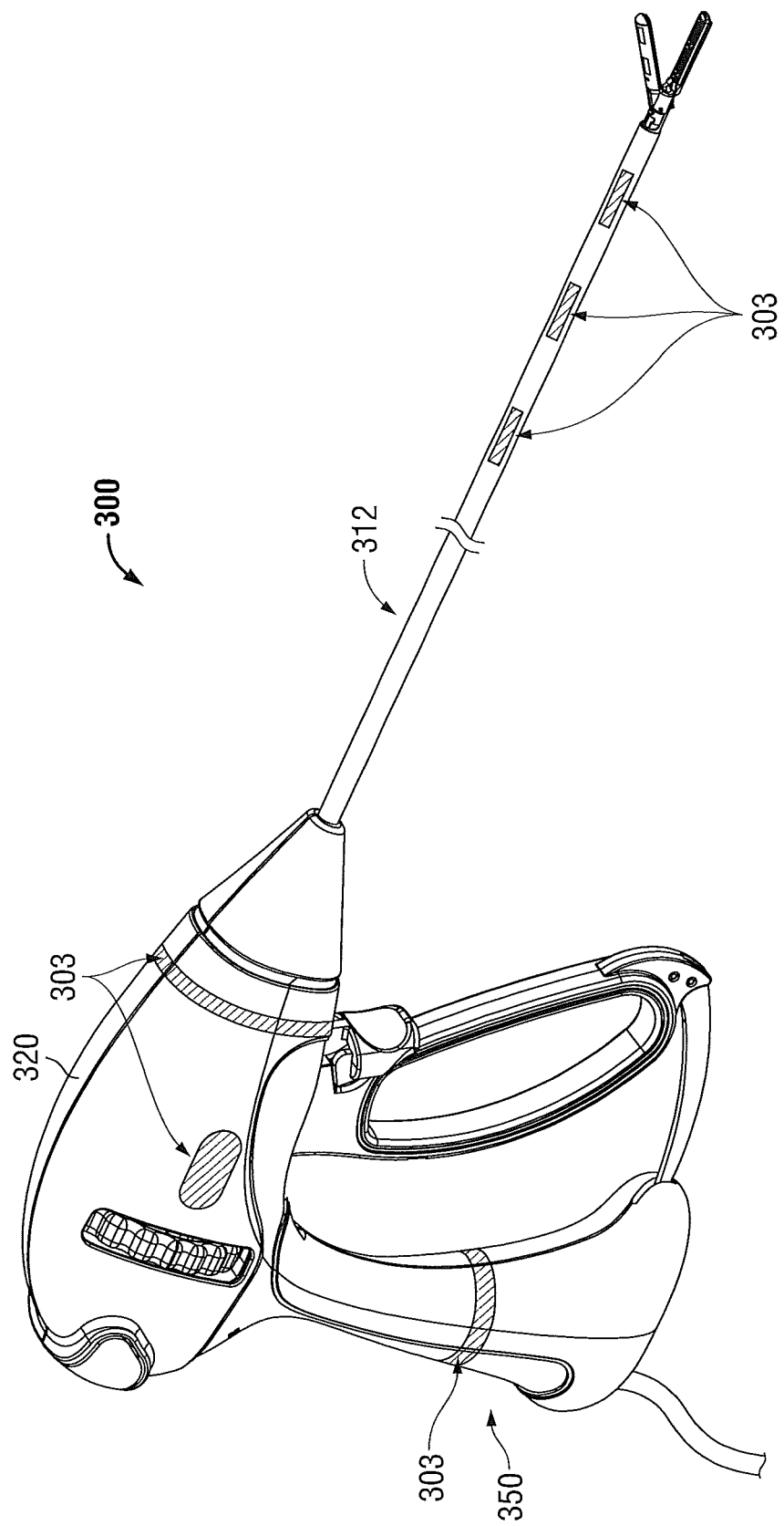
FIG. 3B is a perspective view of the medical device of FIG. 3A, shown in a used condition.

As shown in FIGS. 3A and 3B, a forceps 300 similar to forceps 10 (FIG. 1) is shown including one or more limited-use portions 303. Limited-use portions 303 may be incorporated into outer or externally-disposed components or features of forceps 300. Incorporating limited-use portions 303 into the outer or externally-disposed components of forceps 300 is advantageous in that the externally-visible limited-use portions 303 provide the user with a clear visual indication that forceps 300 is contaminated (or appears contaminated) and should not be used. As discussed in more detail below, limited-use portions 303 may include any suitable contamination trap or indicator such as, but not limited to, blood (or other contamination) traps, blood (or other bodily or surgical fluid) sensitive materials, absorptive materials, etc.

With continued reference to FIGS. 3A and 3B, as mentioned above, forceps 300 is similar to forceps 10 (FIG. 1) and, thus, will not be described in detail herein for purposes of brevity. Limited-use portion 303 may be incorporated into, e.g., formed integrally with, disposed within, or otherwise attached or coupled to, housing 320, shaft 312, fixed handle 350, and/or any other suitable externally-disposed component of medical device 300.

In one embodiment, e.g., prior to use when forceps 300 is in a first state, as shown in FIG. 3A, limited-use portions 303 exhibit an initial appearance in which limited-use portions 303 substantially blend into the surrounding components of forceps 300 or otherwise appear as innocuous portions of forceps 300. As shown in FIG. 3B, after a prescribed use of forceps 300 wherein limited-use portions 303 come into contact with blood, contaminants, fluids, etc., one or more of the limited-use portions 303 are transitioned to a second state to exhibit a used appearance in which the limited-use portions 303 exhibit actual or perceived contamination, e.g., such that the limited-use portions 303 are visibly changed in color, state, appearance, configuration, and/or content, thereby indicating that forceps 300 should no longer be used.

While the above embodiment describes limited-use portion 303 being disposed on an outer surface of the medical device 300, it should be understood that limited-use portions 303 may also or alternatively be disposed on an interior portion of any suitable medical device that is exposed to contamination during use. For example, a compartment trap or oubliette may be formed on the inside of forceps 300 to trap blood or similar bodily fluids. Other embodiments of limited-use portions as described herein may also be employed internally. Particular embodiments of limited-use portions 303 configured to provide the appearance of contamination after use are described in detail below.

Figure 4A:
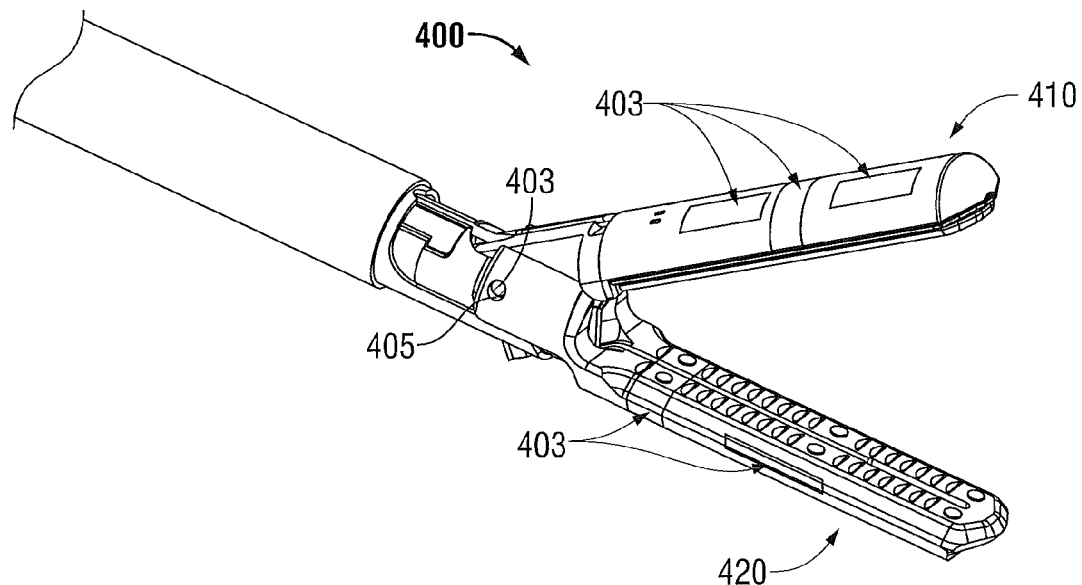
FIG. 4A is a perspective view of an end effector assembly provided in accordance with the present disclosure and configured for use with the medical device of FIG. 1, shown in an unused condition.
Figure 4B:
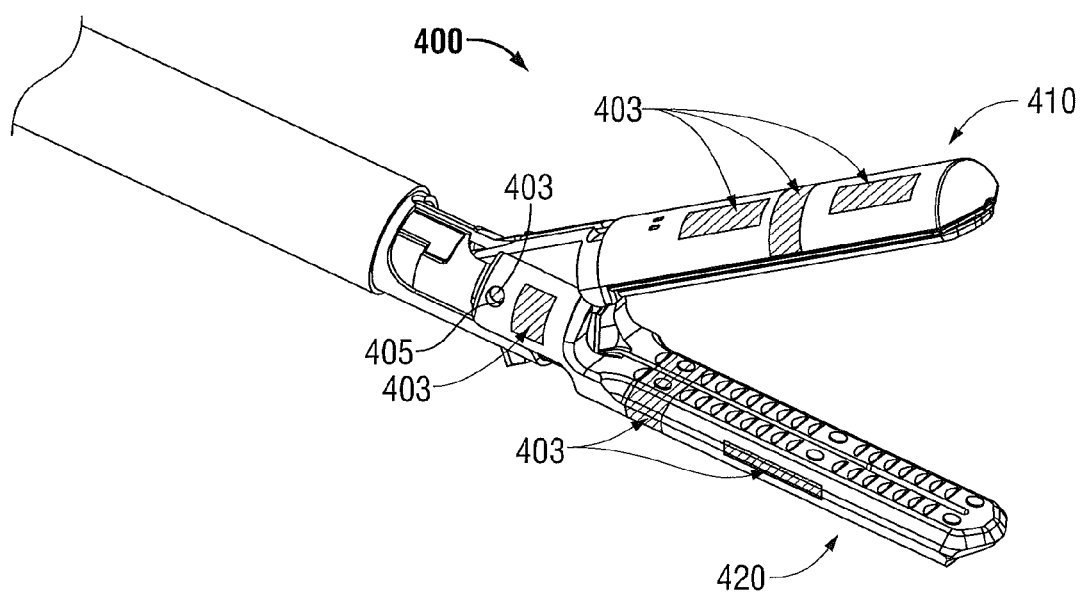
FIG. 4B is an perspective view of the end effector assembly of FIG. 4A, shown in a used condition.

Referring to FIGS. 4A and 4B, an end effector assembly 400 similar to end effector assembly 100 (FIG. 1) and configured for use with forceps 10 (FIG. 1) is shown. As end effector assembly 400 is similar to end effector assembly 100 (FIG. 1), end effector 400 will not be described in detail herein for purposes of brevity. End effector assembly 400 may include one or more limited-use portions 403. Limited-use portions 403, which are included, integrated, or disposed within portions or components of end effector assembly 400, e.g., of either or both of jaw members 410, 420 or portions thereof, are configured such that, once used beyond a prescribed limit (such as, but not limited to, a set amount of uses and/or an amount of time being activated for use), the limited-use portions 403, and hence the end effector assembly 400, appear contaminated beyond a point of safe use, thus inhibiting or cautioning a user from further using end effector assembly 400. A dimension and/or configuration of limited use portions 403 may be modified to define the prescribed limit. Similarly, as described above with respect to forceps 300 (FIGS. 3A-3B), limited-use portions 403 are configured to transition from an first state (FIG. 4A) to a second state (FIG. 4B) after use, e.g., after contact with blood, contaminants, fluids, etc., such that the user is visually alerted to the fact that end effector assembly 400 should no longer be used.

Various embodiments of limited-use portions which may be incorporated into medical devices or components thereof, e.g., as limited-use portions 303, 403 (FIGS. 3A-3B and 4A-4B, respectively), are shown and described below with reference to FIGS. 5A-7. Other suitable configurations are also contemplated. In each of these embodiments, the limited-use portions are configured to trap contaminants, display trapped contaminants or provide an appearance of trapped contaminants, and/or transition to a different state upon contact with blood, tissue, tissue remnants, fluids, and/or any other contaminants or surgical materials encountered during typical use of a surgical device.

Referring to FIGS. 5A and 5B, an embodiment of a limited-use portion 500 including a contamination trap 503 is shown. Limited-use portion 500 includes contamination trap 503 that has grooves 505 for trapping tissue remnants, blood, and other bodily fluids encountered during surgery. The grooves 505 are suitably designed to make sterilization and cleaning exceedingly difficult and provide a clear visual indication of how contaminated the limited-use portion 500 has become after use, e.g., after a surgical procedure. The grooves 505 are simplified representations and do not indicate the only groove configuration disclosed herein. For example, grooves 505 may be misaligned, non-straight, curved, asymmetric, angled towards each other, a patterned feature, and/or walls that are specifically configured to make cleaning difficult.

Referring to FIG. 6, another limited-use portion 600 including a contamination trap 603 having a window 605 covering at least a portion of the contamination trap 603 is shown. Contamination trap 603 extends beyond window 605 on at least one side thereof to allow the passage of fluid and/or solid contaminants into trap 603 while inhibiting at least some fluid and/or solid contaminants from leaving contamination trap 603 once disposed therein. Window 605 allows the user to see into contamination trap 603, while sufficiently obscuring access to contamination trap 603 for cleaning or removal of contaminants. A window similar to window 605 may also be disposed about contamination trap 503 (FIGS. 5A-5B), for similar purposes.

Referring to FIG. 7, another limited-use portion 700 including a contamination trap 703 is shown. Contamination trap 703 includes a sponge-like or otherwise absorptive material configured to soak in contaminants. The sponge-like contamination trap 703 exhibits at least some of the contaminants absorbed therein while also being difficult to clean after contamination from a surgical procedure, thus visually alerting a user to the fact that the device incorporating limited-use portion 700 should no longer be used.

Figure 8:
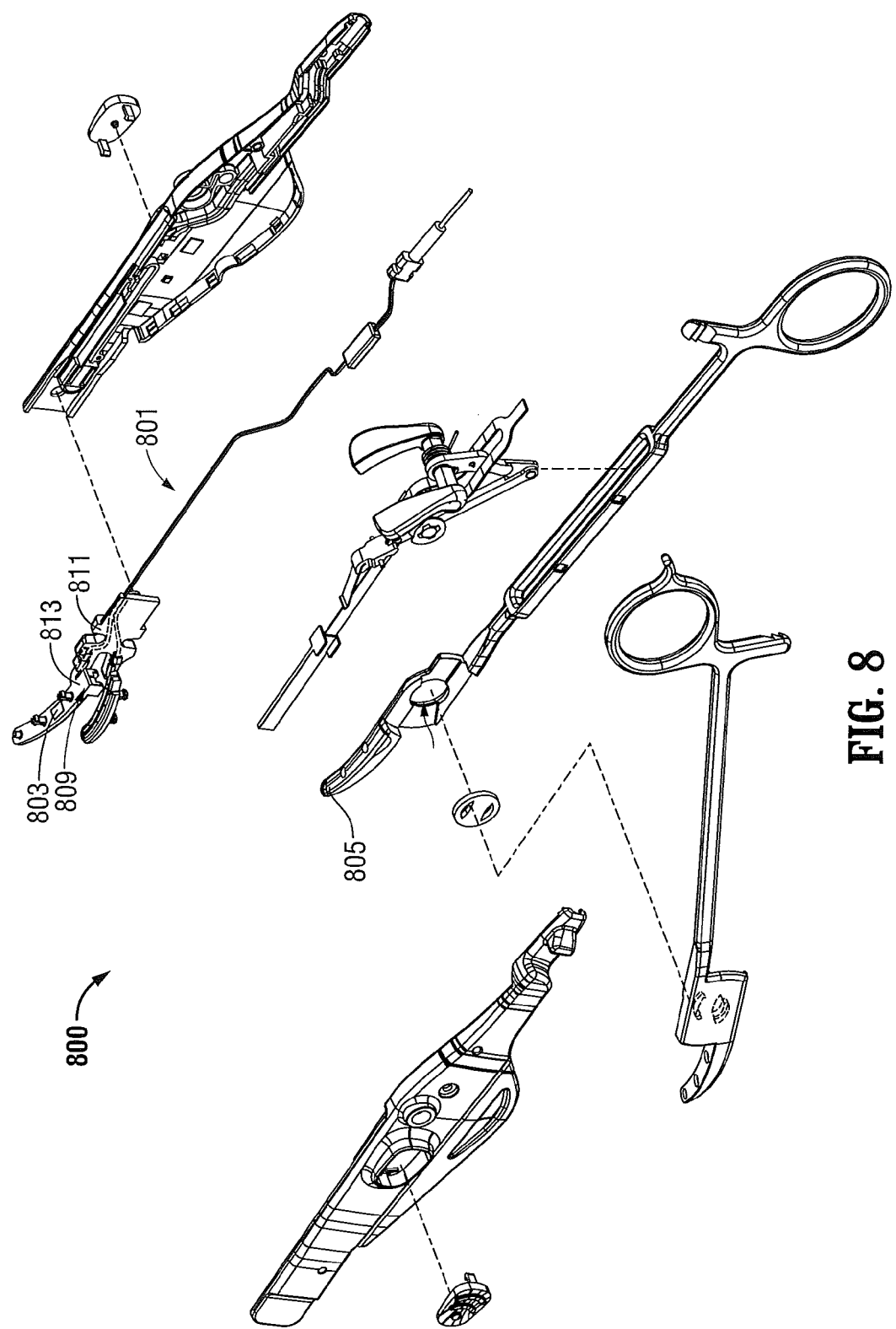
FIG. 8 is a perspective, exploded view of another medical device provided in accordance with the present disclosure.

Referring to FIG. 8, another embodiment of a forceps 800 is shown having a removable electrode assembly 801 with a limited-use portion including a contamination trap 803 disposed thereon. Contamination trap 803 may be configured similar to any of the contamination traps described above. As shown in FIG. 8, the limited-use portion 803 is disposed on an upper portion of electrode 809 of electrode assembly 801 such that the limited-use portion 803 is at least partially sandwiched between jaw member 805 and electrode 809 when the disposable electrode assembly 801 is attached to the forceps 800. In such an embodiment, the contamination trap 803 becomes contaminated during use and forces the user to remove electrode assembly 801 from forceps 800 to attempt to clean contamination trap 803. As contamination trap 803 inhibits cleaning, the user would ultimately be inclined to discard electrode assembly 801 and provide a new electrode for use with forceps 800. Additionally or alternatively, electrode assembly 801 may be configured to break upon removal from the forceps 800, in which case, removing electrode assembly 801 in an attempt to clean contamination trap 803 will break electrode assembly 801 and substantially prohibit reuse of the electrode assembly 801.

As also shown in FIG. 8, a limited-use portion including a heat sensitive material, such as a plastic or polymer, which changes state (e.g., color) to indicate that the device has been used may also be provided. For example, flex joint 811, or electrode substrate 813 may include the heat sensitive material such that changes the appearance of flex joint 811 or substrate 813. Upon changing color, the flex joint 811 or substrate 813 may exhibit an appearance of contamination, e.g., flex joint 811 or substrate 813 or a portion thereof may turn the color of blood or exhibit a contaminant-like pattern. Other portions of the forceps 800 may also include similar features. Likewise, any of the other medical devices described herein or any other suitable medical device may include such features.

The limited-use portions of any or all of the above-described embodiments may also include a sterilization sensitive ink that reveals a message upon an attempt to sterilize the limited-use portion, or after use. For example, flex joint 811 may include a message such as "Do Not Use" that appears after a re-sterilization or use. Any suitable message may be written or engraved with sterilization cycle sensitive materials. Also, a blood-sensitive ink, bodily fluid-sensitive ink, tissue-sensitive ink, etc., may be used to discolor or re-pattern the limited-use portion to make the device appear to be contaminated inhibiting further use.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached figures are presented only to demonstrate certain examples of the disclosure. Other elements, steps, methods and techniques that are insubstantially different from those described above and/or in the appended claims are also intended to be within the scope of the disclosure.

What is claimed is:

1. A medical device, comprising:
    at least one component configured to contact contaminants during use of the medical device; and
    a first limited-use portion associated with the at least one component and configured to transition during use from a first state, wherein the first limited-use portion exhibits a clean appearance, to a second state, wherein the first limited-use portion exhibits a contaminated appearance that visually indicates to a user that the at least one component is not further usable, the first limited-use portion defining a cavity within the at least one component and including a transparent window covering a portion of the cavity to define an opening between the transparent window and an outer surface of the at least one component, the opening configured to allow passage of contaminants therethrough and into the cavity.

2. The medical device of claim 1, wherein the at least one component is a jaw member of a forceps.

3. The medical device of claim 1, wherein the at least one component is a disposable electrode assembly.

4. The medical device of claim 3, wherein the disposable electrode assembly is configured to conduct electrosurgical energy to tissue.

5. The medical device of claim 1, wherein the at least one component is a housing of an endoscopic medical device.

6. The medical device of claim 1, further comprising a second limited-use portion associated with the at least one component.

7. The medical device of claim 6, wherein the second limited-use portion includes a plurality of grooves configured to trap bodily fluids and tissue remnants.

8. The medical device of claim 1, further comprising a second limited-use portion having a color change material associated with the at least one component and configured to transition during use from a first state, wherein the second limited-use portion exhibits a first appearance, to a second state, wherein the second limited-use portion exhibits a second appearance that visually indicates to a user that the at least one component is not further usable.

9. The medical device of claim 8, wherein the color change material is configured to change color upon making contact with at least one of blood, tissue, or fluids.

10. The medical device of claim 8, wherein the color change material is temperature-sensitive such that the color change material changes color in response to a change in temperature.

11. The medical device of claim 1, wherein the transparent window is configured to prevent passage of fluids therethrough.

12. A method, comprising:
providing a medical device including at least one component;
using the medical device to perform a surgical task, wherein, during use of the medical device, a first limited-use portion associated with the at least one component comes into contact with contaminants such that the contaminants are captured within a cavity defined within the at least one component; and
viewing the contaminants captured within the cavity through a transparent window that partially covers the cavity thereby alerting a user that the at least one component is not further usable after use of the medical device,
wherein an opening is defined between the transparent window and an outer surface of the at least one component, and wherein the contaminants move into the cavity via the opening.

13. The method of claim 12, further comprising capturing the contaminants within a plurality of grooves defined in the at least one component, wherein the plurality of grooves is configured to trap bodily fluids and tissue remnants.

14. The method of claim 12, further comprising changing a color of a second limited-use portion associated with the at least one component by contacting the second limited-use portion with the contaminants.

15. The method of claim 12, wherein the transparent window is configured to prevent passage of fluids therethrough.

\* \* \* \* \*